US010099065B2

(12) United States Patent
Pina (10) Patent No.: US 10,099,065 B2
(45) Date of Patent: Oct. 16, 2018

(54) LASER THERAPY APPARATUS AND METHOD

(71) Applicant: CAPILLUS LLC, Coral Gables, FL (US)

(72) Inventor: Carlos Pina, Coral Gables, FL (US)

(73) Assignee: Capillus, LLC, Miami, FL (US)

( * ) Notice: Subject to any disclaimer, the term of this patent is extended or adjusted under 35 U.S.C. 154(b) by 0 days.

(21) Appl. No.: 15/066,435

(22) Filed: Mar. 10, 2016

(65) Prior Publication Data

US 2016/0271420 A1    Sep. 22, 2016

Related U.S. Application Data

(63) Continuation of application No. 14/743,158, filed on Jun. 18, 2015.

(Continued)

(51) Int. Cl.
*A61N 5/06*    (2006.01)
*H05K 1/02*    (2006.01)
(Continued)

(52) U.S. Cl.
CPC .......... *A61N 5/0617* (2013.01); *H05K 1/028* (2013.01); *A61N 2005/067* (2013.01);
(Continued)

(58) Field of Classification Search
CPC ................ A61N 5/0613; A61N 5/0617; A61N 2005/0626; A61N 2005/0627;
(Continued)

(56) References Cited

U.S. PATENT DOCUMENTS

| 6,666,878 B2 * | 12/2003 | Carlgren | A61N 5/0617 607/88 |
| 7,722,656 B1 * | 5/2010 | Segal | A61N 5/0617 607/88 |

(Continued)

FOREIGN PATENT DOCUMENTS

| AU | 2013201772 A1 | 10/2010 |
| AU | 2014202114 A1 | 5/2014 |

(Continued)

OTHER PUBLICATIONS

Extended European Search Report dated Dec. 11, 2015, by the European Patent Office in corresponding European Patent Application No. 15174248.3 (7 pages).

(Continued)

*Primary Examiner* — Ahmed Farah
(74) *Attorney, Agent, or Firm* — Pablo Meles; Espinosa Martinez, PL (57) ABSTRACT

A laser therapy apparatus includes a cap body shell, a printed circuit board, a power supply, and a plurality of light sources electrically coupled to the printed circuit board and powered by the power supply. The plurality of light sources includes at least one laser diode. The printed circuit board includes a plurality of cuts, each cut including at least two sides. The printed circuit board is also bent into a dome shape. A laser therapy apparatus may also include at least two photodiode proximity sensors configured such that the plurality of light sources will only light if both photodiode proximity sensors are within a predetermined distance of a scalp to be treated, and the plurality of light sources will turn off if either of the at least two photodiode proximity sensors is moved more than a predetermined distance away from the scalp.

15 Claims, 9 Drawing Sheets

Related U.S. Application Data (60) Provisional application No. 62/136,195, filed on Mar. 20, 2015.

(51) Int. Cl.
*H05K 1/18* (2006.01)
*A61N 5/067* (2006.01)

(52) U.S. Cl.
CPC .............. *A61N 2005/0647* (2013.01); *A61N 2005/0652* (2013.01); *A61N 2005/0663* (2013.01); *H05K 1/189* (2013.01); *H05K 2201/09063* (2013.01); *H05K 2201/10121* (2013.01)

(58) Field of Classification Search
CPC .... A61N 2005/0628; A61N 2005/0635; A61N 2005/0643; A61N 2005/0647; A61N 2005/0651; A61N 2005/0652; A61N 2005/067; H05K 1/028; H05K 1/0284; H05K 1/189
USPC .......................... 607/88–91, 93, 94; 128/898
See application file for complete search history.

(56) References Cited

U.S. PATENT DOCUMENTS

| | | | | |
|---|---|---|---|---|
| 2004/0153131 | A1* | 8/2004 | Yorke | A61N 5/0617 607/91 |
| 2006/0095099 | A1* | 5/2006 | Shanks | A61N 5/0617 607/89 |
| 2007/0256212 | A1 | 11/2007 | Rabin | |
| 2008/0114418 | A1 | 5/2008 | Myeong et al. | |
| 2010/0106077 | A1* | 4/2010 | Rabin | A61N 5/0616 604/20 |
| 2010/0242155 | A1* | 9/2010 | Carullo, Jr. | A61N 5/0617 2/171.2 |
| 2011/0092863 | A1 | 4/2011 | Kim et al. | |
| 2012/0059440 | A1 | 3/2012 | Hamid | |
| 2012/0130455 | A1 | 5/2012 | Baird et al. | |
| 2013/0190845 | A1* | 7/2013 | Liu | A61N 5/0616 607/90 |
| 2014/0063794 | A1* | 3/2014 | Parekh | F21S 8/04 362/185 |
| 2014/0194966 | A1 | 7/2014 | Babero Castro | |
| 2014/0316492 | A1* | 10/2014 | Min | A61N 5/0613 607/91 |
| 2015/0005854 | A1 | 1/2015 | Said | |
| 2015/0297914 | A1* | 10/2015 | Hamid | A61N 5/0617 607/89 |
| 2017/0333730 | A1* | 11/2017 | Hamid | A61N 5/0617 |

FOREIGN PATENT DOCUMENTS

| | | |
|---|---|---|
| AU | 2013201771 A1 | 10/2014 |
| EP | 3069762 A1 | 9/2016 |
| WO | WO 2009/021225 A1 | 2/2009 |
| WO | WO 2010/110861 A1 | 9/2010 |
| WO | WO 2012/145853 A2 | 11/2012 |
| WO | 2016153926 A1 | 9/2016 |

OTHER PUBLICATIONS

International Search Report and Written Opinion issued by the International Searching Authority dated Jun. 22, 2016 in corresponding International Application No. PCT/US2016/022903 (12 pages).

Canadian Examiner's Report dated Feb. 13, 2017 in Canadian Application No. 2,924,152 (3 PGS).

Examination Report issued by the Australian Patent Office in Application No. 2015215851 dated Dec. 9, 2016 (4 PGS).

Office Action/Examination Search Report dated Feb. 13, 2017, by the Canadian Patent Office in corresponding Canadian Patent Application No. 2,924,152. (3 pages).

Second Examination Report issued by the Australian Patent Office dated May 2, 2017 in corresponding Australian Application No. 2015215851 (3 pages).

* cited by examiner

LASER THERAPY APPARATUS AND METHOD

CROSS-REFERENCE TO RELATED APPLICATION

This application claims priority under 35 U.S.C. § 119(e) to U.S. provisional Application No. 62/136,195, filed on Mar. 20, 2015, and non-provisional application Ser. No. 14/743,158, filed on Jun. 18, 2015, the entire contents of which are incorporated herein by reference thereto.

TECHNICAL FIELD

The application relates to the field of laser therapy, in particular low-level laser therapy (LLLT) for promoting hair growth.

BACKGROUND

Hair diseases, including hair loss (alopecia), baldness, withered hair, white hair, and so forth, are common, and can be distressing. Methods for treating such hair diseases include topical drugs, ingestible medications, and surgery (for example, through implantation of hair plugs to replace missing hair). However, these methods may require a lengthy and arduous course of treatment, may be expensive, and may not be effective. Topical drug treatments may require that the person must be treated in a specific location, which can be inconvenient. Further, long-term use of such treatments may yield toxic side effects, cause scalp injury, and otherwise affect the health of the individual receiving treatment.

It is desirable to find improved methods and apparatuses for promoting hair growth.

SUMMARY

In embodiments, a laser therapy apparatus includes a cap body shell, at least one printed circuit board disposed within the cap body shell, a power supply, and a first plurality of light sources electrically coupled to the printed circuit board and powered by the power supply. The first plurality of light sources may comprise at least one laser diode. The at least one printed circuit board may comprise a plurality of cuts, such as curved or angled cuts, each cut having at least two sides, such as at least three sides, or at least four sides, and may be bent into a dome shape. The laser therapy apparatus may further include at least two photodiode proximity sensors disposed within the cap body shell. The photodiode proximity sensors may be configured such that the first plurality of light sources will only light if both photodiode proximity sensors are within a predetermined distance from a scalp to be treated, and such that the first plurality of light sources will turn off if either of the at least two photodiode proximity sensors is moved more than the predetermined distance away from the scalp to be treated.

In embodiments, a laser therapy apparatus may include a cap body shell, at least one printed circuit board, a power supply, and a first plurality of light sources electrically coupled to the power supply, where the first plurality of light sources includes at least one laser diode and at least one light emitting diode. The at least one printed circuit board may comprise a plurality of cuts, such as curved or angled cuts, each cut having at least two sides, and may be bent into a dome shape. The laser therapy apparatus may further include at least two photodiode proximity sensors disposed within the cap body shell. The photodiode proximity sensors may be configured such that the first plurality of light sources will only light if both photodiode proximity sensors are within a predetermined distance from a scalp to be treated, and such that the first plurality of light sources will turn off if either of the at least two photodiode proximity sensors is moved more than the predetermined distance away from the scalp to be treated.

In embodiments, a printed circuit board for a laser therapy apparatus includes a plurality of cuts, where the cuts are spaced to facilitate bending the printed circuit board into a dome shape. In embodiments, the cuts in the plurality of cuts are selected from the group consisting of curved cuts, angled cuts, and combinations thereof.

BRIEF DESCRIPTION OF THE FIGURES

FIG. 7 illustrates one embodiment of a hat including a laser therapy apparatus, including a slit allowing a wire connecting the laser therapy apparatus to the power supply to pass through.

DETAILED DESCRIPTION

Glossary of Terms

Laser Diode—a laser diode is a semiconductor laser with an active laser medium formed by a p-n junction of a semiconductor diode.

Light Emitting Diode (LED)—a light-emitting diode is a semiconductor light source, in particular a p-n junction diode that emits light when activated.

Printed Circuit Board—a printed circuit board is a sheet which mechanically supports and electrically connects electronic components.

Photodiode Proximity Sensor—A photodiode is a semiconductor device that converts light into current. A photodiode proximity sensor is a sensor comprising such a semiconductor device, which operates to detect a distance to an object by measuring the intensity of the light reflected back onto the photodiode by the object.

Described herein is a laser therapy apparatus, and a printed circuit board for use in such a laser therapy apparatus, and a method of using a laser therapy apparatus. In the following description, numerous specific details are set forth in order to provide a thorough understanding of various embodiments of the laser therapy apparatus, printed circuit board, and method. It will be apparent, however, to one skilled in the art that embodiments herein may be practiced without some or all of these specific details. In other instances, well known steps and/or structures have not been described in order to not unnecessarily obscure the laser therapy apparatus, printed circuit board, and method.

Unless otherwise indicated, all numbers expressing quantities, conditions, and the like in the instant disclosure and claims are to be understood as modified in all instances by the term "about." The term "about" refers, for example, to numerical values covering a range of plus or minus 10% of the numerical value. The modifier "about" used in combination with a quantity is inclusive of the stated value.

In this specification and the claims that follow, singular forms such as "a", "an", and "the" include plural forms unless the content clearly dictates otherwise.

Figure 1:
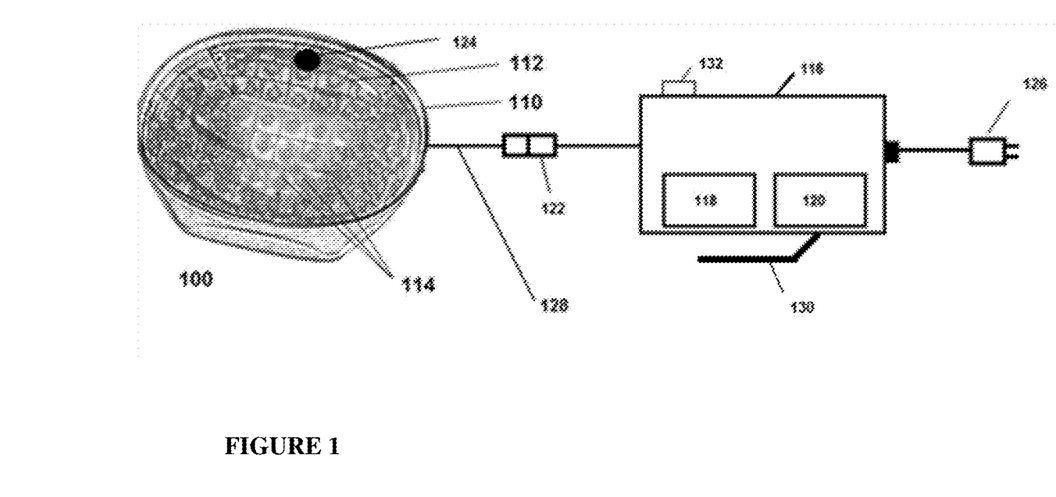
FIG. 1 illustrates a laser therapy apparatus according to one embodiment of the disclosure.

In embodiments, the laser therapy apparatus according to the present disclosure may be a cap adapted to fit on the human head. FIG. 1 illustrates an exemplary laser therapy apparatus according to one embodiment of the present disclosure. The laser therapy apparatus includes a cap body shell 110, a printed circuit board 112, and at least one light source 114 or at least a first plurality of light sources 114. In embodiments, laser therapy apparatus further includes a headband for fitting the cap body shell to the head of a user and holding the laser therapy apparatus in place. A decorative outer shell (not shown) can be added to give the cap body shell 110 the appearance of a regular hat, such as a baseball cap, brimmed hat, knit hat, or virtually any other type of hat.

In embodiments, the cap body shell is hemispherical or nearly hemispherical in shape.

Figure 2:
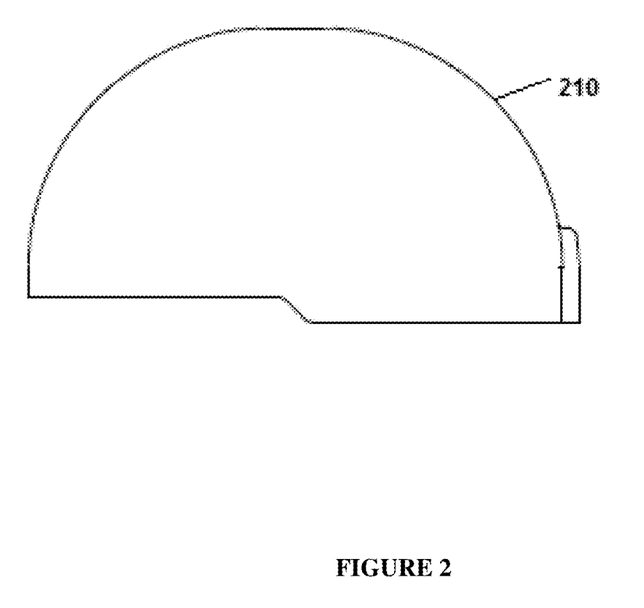
FIG. 2 illustrates a cap body shell having a predetermined size.

In embodiments, the cap body shell is specifically sized to fit a head of a predetermined size, and multiple predetermined sizes may be available to fit different sizes of heads. For example, as shown in FIG. 2, in embodiments, a cap body shell 210 may be a hemispherical or nearly hemispherical shell of a predetermined size, where the specific predetermined size may be selected to fit a particular size of head, and multiple predetermined sizes may be available to fit different sizes of heads.

Figure 3A:
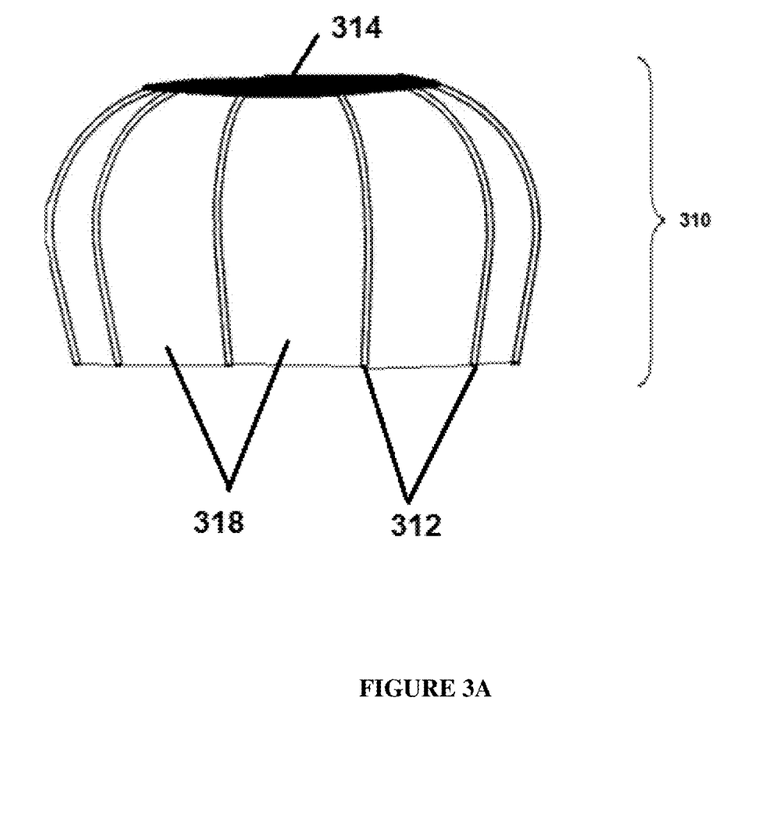
FIGS. 3A and 3B illustrate a cap body shell adjustable to fit a variety of head sizes.
Figure 3B:
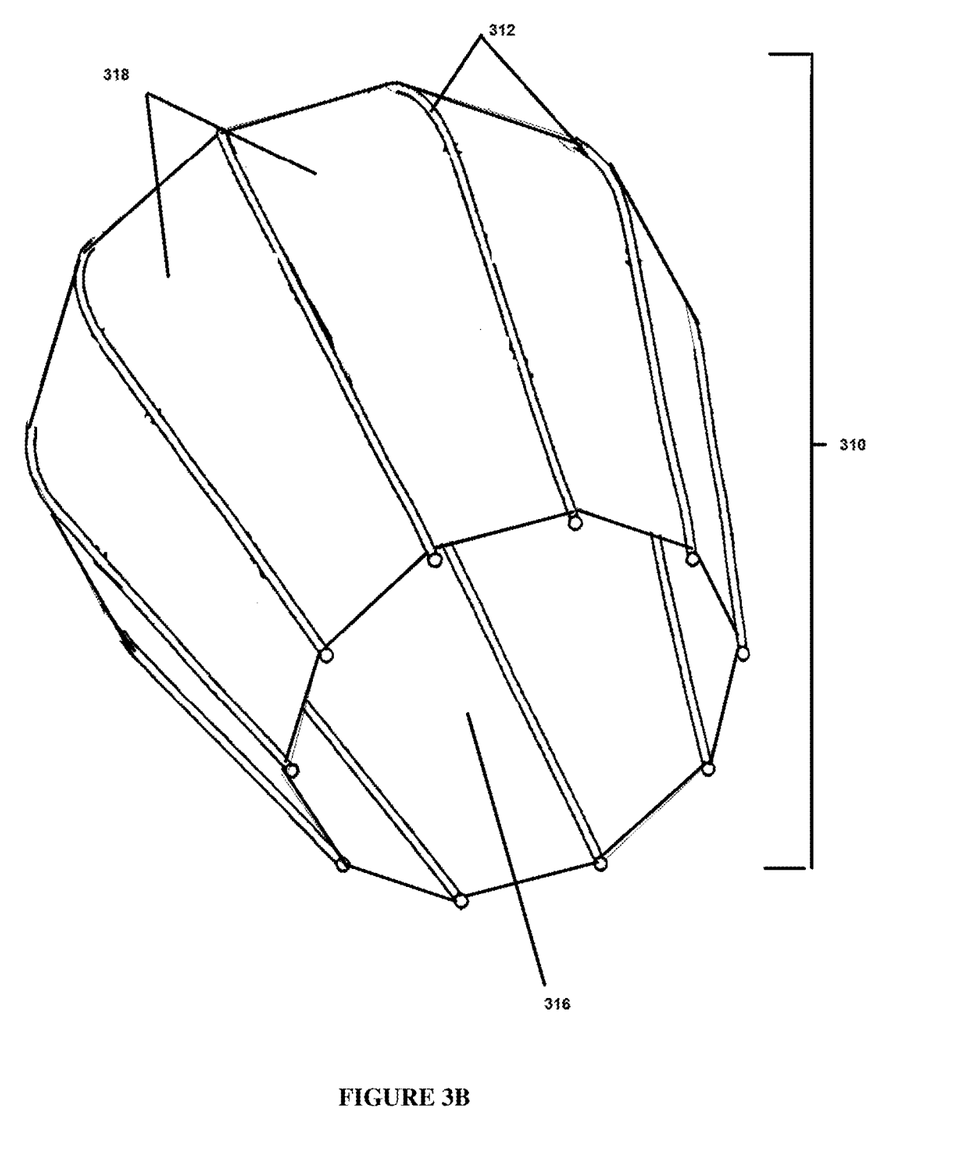

In other embodiments, a single cap body shell may be adjustable to fit a variety of sizes of heads. For example, as shown in FIGS. 3A and B, in embodiments, a cap body shell 310 may be structured to allow for the varying the internal volume of the cavity within the cap body shell 310, such that the cap body shell 310 may be adjusted to fit heads of different sizes (e.g., a one-size-fits-all or one-size-fits-most cap body shell). In embodiments, an adjustable cap body shell 310 may comprise a plurality of resilient fingers 312 fixably attached to a base portion 314 such that the fingers define an open cavity shaped to accommodate a human head, where a user may place their head into the cavity through an opening 316 in the fingers 312. In embodiments, the opening 316 is smaller than the size of the head inserted therein, such that the fingers 312 flexibly deform around the head and apply gentle pressure to hold the cap body shell 310 in place around the head. In embodiments, the resilient fingers 312 may be pliable, such as to adjust the size of the opening 316. For example, in embodiments, the resilient fingers 312 may be made out of metal strips or metal wire, where the metal may be, for instance, a pliable metal such as copper.

In embodiments, the resilient fingers 312 are connected via a material 318. In embodiments, the material 318 is opaque, so as to reduce and/or eliminate the amount of light from the plurality of light sources that is visible when looking at the laser therapy apparatus while in use. In embodiments, the material 318 is a conforming, flexible, and/or elastic material. For example, in embodiments, the material 318 may be, for example, woven or non-woven fabric, knitted material, elastic, spandex, rubber, mesh, foam rubber, and/or some combination thereof. For example, in embodiments, the material 318 may be a resiliently stretchable material such as, for example, lycra, spandex, polyester, nylon, rayon, cotton, or a combination thereof. In embodiments, the material 318 may be a stretchable material capable of stretching an additional 5 to 75% such as an additional 10 to 60%, or an additional 20 to 50%, or an additional 40 to 50%, beyond the material's original dimensions while being able to return to the material's original shape/dimensions.

In embodiments, the stretchable material 318 extends continuously around the cap body shell 310, surrounding and optionally enclosing the resilient fingers 312. In other embodiments, the stretchable material is present as panels between the resilient fingers 312. In embodiments, as a laser phototherapy apparatus is placed on a user's head and the fingers 312 of the cap body shell 310 flexibly deform around the head, the material 318 stretches to accommodate the expansion of the fingers 312. When the laser phototherapy apparatus is removed and the fingers 312 return to their original position, the material 318 returns to its original dimensions.

In embodiments, the printed circuit board is bent into a dome shape to fit within the cap body shell and to conform to the contours of a human head, so that the laser therapy apparatus may precisely target an affected area for treatment. In embodiments, the printed circuit board 112 includes a plurality of cuts which are spaced to facilitate shaping the printed circuit board into a dome shape that conforms to the contours of a human head. In embodiments, the plurality of cuts may comprise at least two cuts, such as at least three cuts, or at least four cuts, or at least five cuts, or at least six cuts, or at least eight cuts, or at least nine cuts. In embodiments, the plurality of cuts may include curved cuts, angled cuts, non-curved, non-angled cuts, and/or combinations thereof. For example, inn embodiments, the plurality of cuts may comprise at least two angled cuts, such as at least three angled cuts, or at least four angled cuts, or at least five angled cuts, or at least six angled cuts, or at least eight angled cuts, or at least nine angled cuts. The perimeter of each cut may contain at least 4 sides/edges, such at least 6 sides, or at least 8 sides, or at least 10 sides.

In embodiments, the laser therapy apparatus may contain one printed circuit board, which may be bent into a dome shape that conforms to the contours of the human head. In other embodiments, the laser therapy apparatus may contain more than one printed circuit board, such as at least two printed circuit boards, or at least three printed circuit boards, or at least four printed circuit boards. In embodiments containing more than one printed circuit board, the printed circuit boards may be connected together or otherwise combined, and configured such that when the printed boards are connected/combined, they form a dome shape that conforms to the contours of the human head. In embodiments containing more than one printed circuit board, each printed circuit board may include cuts, as described above, to facilitate shaping the printed circuit boards into a dome shape.

Figure 4A:
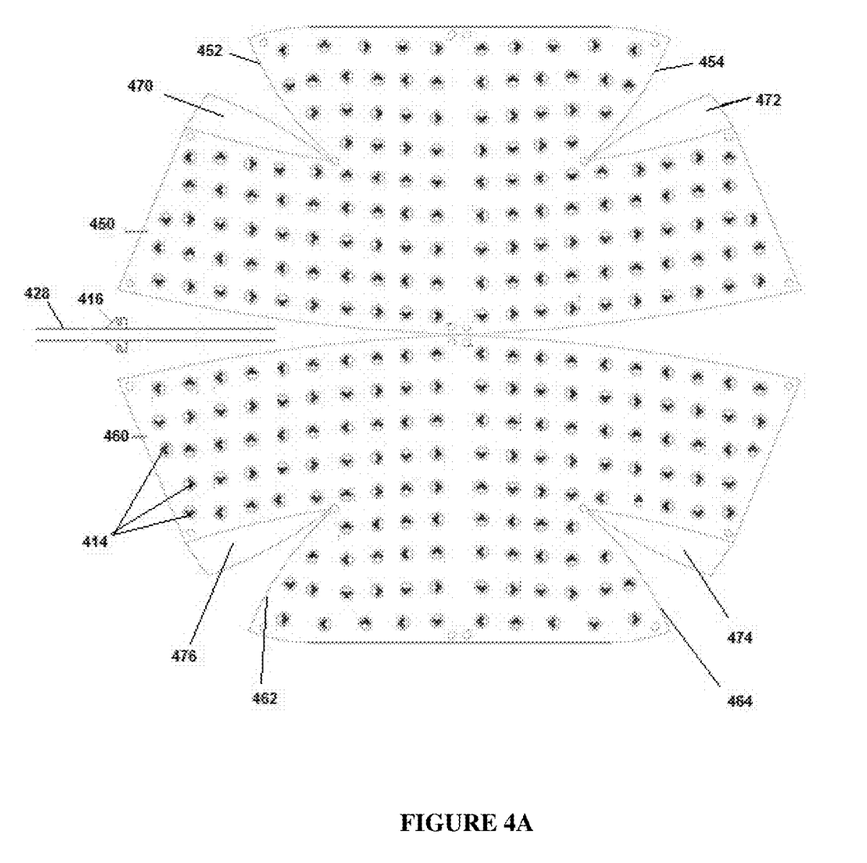
FIG. 4A illustrates an embodiment in which two printed circuit boards (each printed circuit board including two curved cuts) are connected.

FIG. 4A illustrates an embodiment in which a first printed circuit board 450 and a second printed circuit board 460 are connected and bent into a dome shape. In embodiments, the printed circuit board 450 and the printed circuit board 460 are the same. To facilitate bending the first printed circuit board 450 and the second printed circuit board 460 into a dome shape, the first printed circuit board 450 includes curved cuts 452, 454 and the second printed circuit board 460 includes curved cuts 462, 464, where the cuts are spaced to facilitate shaping the first and second printed circuit boards 450, 460 into a dome shape when connected, such that the connected and bent printed circuit boards 450, 460 fit to the contours of a human head. In embodiments, the printed circuit boards 450, 460 may include areas of overlap 470, 472, 474, 476 when bent into a dome shape. In embodiments, light sources 414 are disposed on the first printed circuit board 450 and the second printed circuit board 460. In embodiments, a wire 428 may be used to connect the light sources 414 to a power supply (not pictured). In embodiments, the wire 428 may be held within a wire holder 416.

Figure 4B:
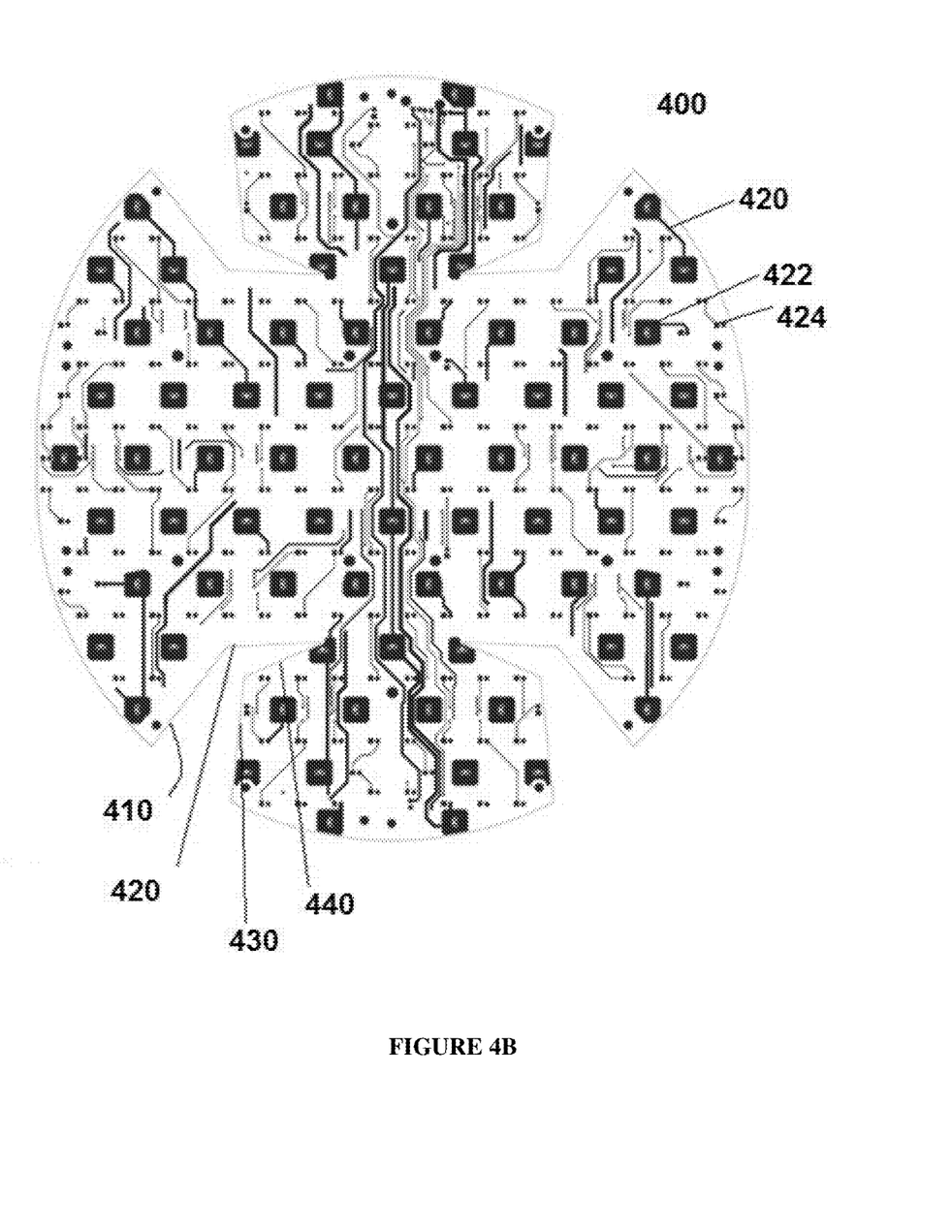
FIG. 4B illustrates an embodiment of a printed circuit board containing four angled cuts, where each angled cut is dogleg shaped.

FIG. 4B illustrates one embodiment of a printed circuit board 400, including printed circuits 420, laser diodes 422, and LEDs 424, containing four angled cuts, where the perimeter of each angled cut has four sides/edges 410, 420, 430, 440, forming a dogleg shape. The cuts are spaced to facilitate shaping the printed circuit board into a dome shape, such that it fits to the contours of a human head.

Figure 5:
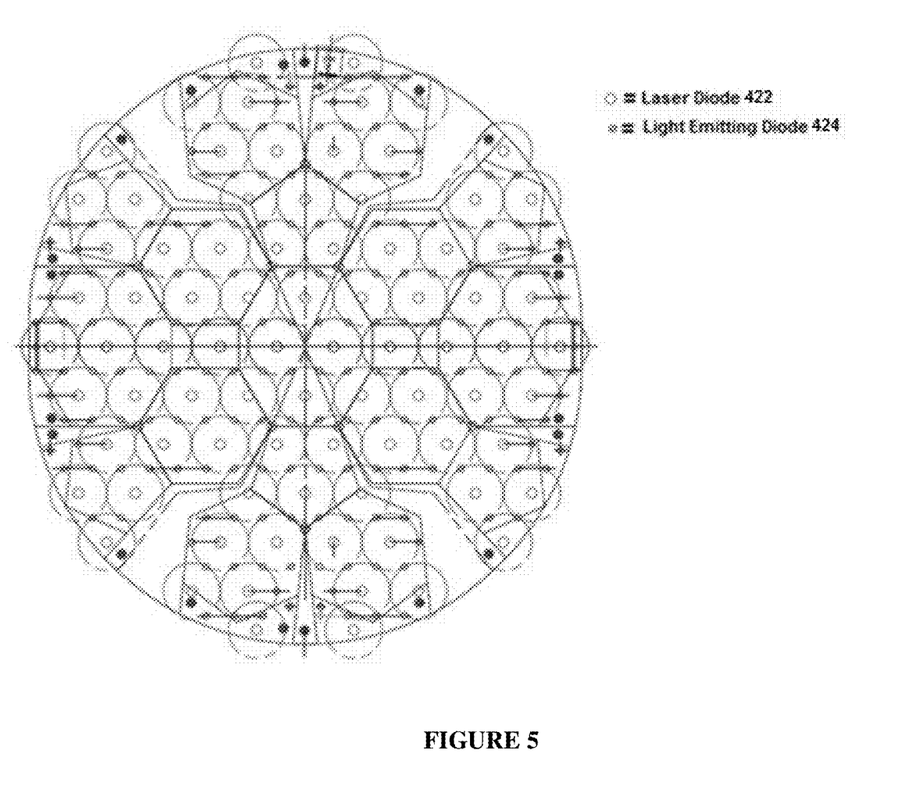
FIG. 5 illustrates an embodiment of a printed circuit board containing four angled cuts and four non-angled cuts.

In embodiments, the printed circuit board may comprise at least one non-angled cut having only two sides, such as at least two non-angled cuts, or at least four non-angled cuts, or at least six non-angled cuts. In embodiments, the printed circuit board comprises curved and/or angled cuts, as well as non-curved, non-angled cuts. FIG. 5 illustrates one embodiment of a printed circuit board comprising both angled cuts and non-curved, non-angled cuts—in particular, in FIG. 5, the printed circuit board contains four angled cuts and four non-curved, non-angled cuts.

In embodiments, the light sources 114 may be set up in parallel. In embodiments, the light sources 114 on the printed circuit board 112 in the cap body shell 110 are connected to a power and control unit 116, where the power and control unit 116 may include a controller 118 and/or a power supply 120. In embodiments, the power supply 120 and/or the controller 118 may be disposed outside the power and control unit 116, such as within the cap body shell 110. In other embodiments, the power supply and/or the controller may be disposed outside of the cap body shell 110. In embodiments, the controller 118 controls the power supply 120, and the controller-controlled power supply provides power for the light sources 114.

In embodiments, the power supply 120 is a rechargeable or a disposable battery, and/or an AC power supply or a DC power supply. In embodiments, the power supply may be a rechargeable battery, where the rechargeable battery may be recharged by disconnecting the battery 120 from the laser therapy apparatus and connecting the battery 120 to an AC or DC power supply via a transformer with a plug 126, which may be connected and disconnected from the battery 120 and/or the power and control unit 116.

In embodiments, the power supply 120 may be a rechargeable battery, where the rechargeable battery may be recharged by first disconnecting the laser therapy apparatus from the power supply 120 by disconnecting a connector 122 disposed on a wire 128 between the light sources 114 and the power supply 120.

In embodiments, the power supply 120 may be a rechargeable battery, where the rechargeable battery may be recharged by connecting the battery to an AC or DC power supply via a plug 126 without requiring disconnection of the battery from the rest of the laser therapy apparatus (e.g., light sources 114). In these embodiments, the laser therapy apparatus may comprise a safety switch which prevents the at least one light source of the laser therapy apparatus from lighting while the laser therapy apparatus is connected to the AC or DC power supply. In this way, there is less danger that the user can be harmed by shock, for example, by attempting to use the device 100 in a wet environment while connected to a 120V, 15 amp AC power supply.

In embodiments, the power and control unit 116 may be a battery pack, which may be disposed within, on, or outside of the cap body shell. In embodiments, the power and control unit may be a battery pack that is external to the cap body shell, and may be carried by a user or clipped to a belt or pant waist using, for example, a belt clip 130.

In embodiments, the light source may be a laser diode, or a light emitting diode, or a combination of laser diodes and light emitting diodes. In embodiments, the controller 118 controls the power supply 120 to provide power for the light sources 114, which provide light to the user's scalp. In embodiments, the light sources of the laser therapy apparatus operate at wavelengths in the visible light range from 380-700 nm, such as from about 600 to about 700 nm, or from about 650 to about 680 nm, such as 650 nm, or 678 nm. In embodiments, the laser diodes emit 650 nm±5 nm light to irradiate a scalp. The laser diodes provide a beam of coherent radiation, while the light emitting diodes provide more general and even light to stimulate the scalp. In embodiments, the laser therapy apparatus may contain multiple light sources, where each light source maybe controlled independently, allowing different patterns to be made with the light sources—thus, the particular light source pattern can be customized for a particular treatment, or to target a particular area of the scalp. In embodiments, the light sources may comprise multiple panels of light sources, where each panel is separately controllable from the other panels, allowing different patterns to be made with the light sources, which can be customized for a particular treatment or to target a particular area of the scalp. In embodiments, the laser therapy apparatus includes a total of at least about 50 light sources, such as at least about 75 light sources, or at least about 100 light sources, or at least about 150 light sources, or at least about 200 light sources, or at least about 250 light sources, or at least about 270 light sources, or at least about 300 light sources, such as from about 100 to about 300 total light sources, or from about 200 to about 280 total light sources, or from about 250 to about 275 total light sources, or from about 270 to about 273 light sources. By including a greater number of light sources (for example, 272 light sources in one embodiment), a greater amount of light may be provided to irradiate a user's scalp. Moreover, by including a large number of light sources, a greater number of permutations of light patterns may be provided, allowing for more tailored targeting of treatment for a particular user.

The light sources may be all the same, or some combination of different light sources. For example, in embodiments, the light sources may be laser diodes, or LEDs, or a combination of laser diodes and LEDs. For instance, in embodiments, the laser therapy apparatus may contain at least about 50 laser diodes, such as at least about 70 laser diodes, or at least about 80 laser diodes, or at least about 150 laser diodes, or at least about 200 laser diodes, or at least about 250 laser diodes, such as from about 50 to about 300 laser diodes, or from about 80 to about 290 laser diodes, or from about 150 to about 275 laser diodes. In embodiments, the laser therapy apparatus may contain light emitting diodes, either alone or in combination with laser diodes. For example, the laser therapy apparatus may contain at least 50 light emitting diodes, such as at least about 70 light emitting diodes, or at least about 80 light emitting diodes, or at least about 150 light emitting diodes, or at least about 200 light emitting diodes, or at least about 250 light emitting diodes, such as from about 50 to about 300 light emitting diodes, or from about 80 to about 290 light emitting diodes, or from about 150 to about 275 light emitting diodes. For example, FIG. 5 illustrates one embodiment of a printed circuit board connected to 272 light sources, in particular, 82 laser diodes and 190 light emitting diodes. In embodiments, the light sources are evenly distributed across the printed circuit board, but different patterns are contemplated, for instance, to mimic male pattern baldness.

In embodiments, the laser therapy apparatus includes at least two photodiode proximity sensors 124. For example, in embodiments, the laser therapy apparatus may contain at least three photodiode proximity sensors, or at least four photodiode proximity sensors, or at least six photodiode proximity sensors. In embodiments, the photodiode proximity sensors 124 may be disposed within the cap body shell. For example, in one embodiment, the laser therapy apparatus contains two photodiode proximity sensors 124 disposed opposite each other in the cap body shell. In embodiments, the at least two photodiode proximity sensors 124 may be configured to be separated by at least the width of four fingers of an average human hand so that someone picking up the cap cannot cover both (or more) of the sensors. The photodiode proximity sensors 124 are electronically connected to the controller, which may be configured such that the plurality of light sources will only light if both photodiode proximity sensors 124 are within a predetermined distance from a scalp to be treated. That is to say, the light from the light sources 114 may be considered harmful or uncomfortable if directly viewed, and the photodiode proximity sensors 124 function to only allow the light sources to light if the proximity sensors are covered within a certain predetermined distance from a scalp being treated. For example, the photodiode proximity sensors 124 may be configured such that the light sources will only light if the photodiode proximity sensors are less than 2 inches away from the scalp, or less than 1 inch away from the scalp, or less than 0.5 inches away from the scalp. Other types of proximity sensors, such as capacitive sensors or tactile sensors, may also be used.

Conversely, the photodiode proximity sensors keep the light sources from lighting if the laser therapy apparatus is moved away from the scalp being treated, thereby preventing accidentally looking directly at the light sources while in use. For example, if either of the at least two photodiode proximity sensors is disposed more than about 0.5 inches away from a scalp, such as more than about 1 inch away from a scalp, or more than about 1.5 inches away from a scalp, or more than about 2 inches away from a scalp, the photodiode proximity sensors will prohibit the light sources from lighting. Thus, if a user removes the laser therapy apparatus from the head without first turning the light sources off, the photodiode proximity sensors will turn the light sources off as soon as at least one of the at least two sensors is moved more than a predetermined distance away from the scalp to be treated.

Figure 6:
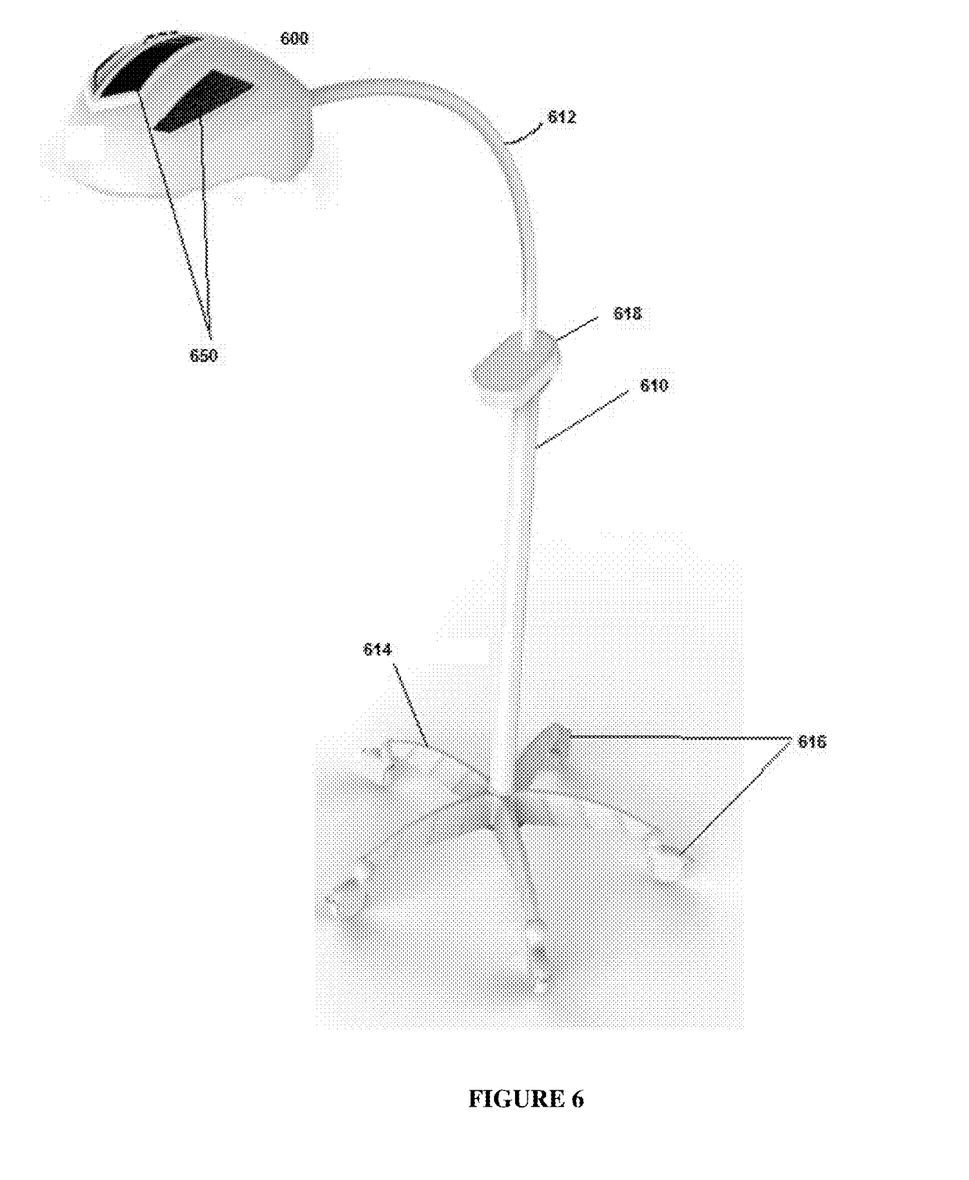
FIG. 6 illustrates one embodiment of a laser therapy apparatus disposed on a stand.

In embodiments, the laser therapy apparatus 600 may be disposed on a stand 610, as shown in FIG. 6. In embodiments, the power supply may be disposed within the stand 610. In embodiments, the stand 610 may include a control panel 618. The cap body shell may be adjustably positioned on the stand 610, or the stand 610 itself may be adjustable, e.g., by an articulated section 612, to facilitate positioning the laser therapy apparatus close to the head of a user. In embodiments, the stand 610 may be disposed on a base 614. In embodiments, the base 614 may include at least one wheel 616, such as at least 2 wheels, or at least 3 wheels, or at least 4 wheels, or at least 5 wheels, or at least 6 wheels.

In embodiments, the laser therapy apparatus includes at least one clear window 650 in the laser therapy apparatus 600, so that light from the pattern of the light sources (not shown) can be viewed while the device is in use and the laser therapy apparatus is disposed on a user's head to indicate the light sources are on, and in some embodiments that the desired light pattern or sequence of light patterns is operating correctly. Although depicted on a laser therapy apparatus 600 disposed on a stand 610, it is contemplated that a hands-free embodiment of the laser therapy apparatus may also include at least one clear window 650.

Figure 7:
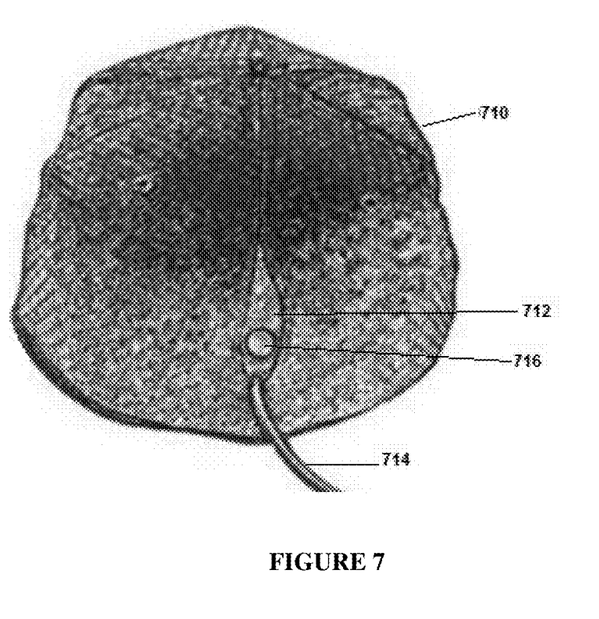

In embodiments, the laser therapy apparatus is a portable, hands-free apparatus. The laser therapy apparatus may be contained within a hat, such as a baseball cap, such that the laser therapy apparatus appears to be a normal hat. A person may therefore receive laser therapy treatment nearly anywhere, including in public, without it being immediately apparent that the hat contains a laser therapy apparatus. Moreover, the hands-free design allows the user to use the apparatus while performing every day activities. In embodiments where the power supply is outside of the cap body shell, a hat 710 may include a slit 712 to allow a wire 714 connecting the laser therapy apparatus to the power supply to pass through, as shown in FIG. 7. In embodiments, the laser therapy apparatus may further include an emission indicator 716. In embodiments, the emission indicator 716 includes a clear grommet (strain relief) which allows light to show through when the light sources 114 are lit and treatment is in progress (in embodiments, the light will be blinking), and the wire 714 passes through as with a strain relief. In embodiments, the emission indicator 716 is an emission indicator light which is configured to turn on or blink when the light sources 114 are lit and treatment is in progress.

In use, the laser therapy apparatus may be placed in proximity with a scalp to be treated. The laser therapy apparatus may then be turned on, such as by a switch 132, power may be supplied to the at least one light source, and the scalp may be irradiated by the at least one light source (e.g., the at least one laser diode and/or the at least one light emitting diode). In embodiments, the switch 132 may be disposed on or within the power and control unit 116. In other embodiments, the switch 132 may be disposed on the cap body shell, on the stand 610, or on the control panel 618 on the stand 610.

In embodiments, the laser diodes emit 650 nm±5 nm light. The irradiation may continue for about 30 minutes, such as from about 20 minutes to about 40 minutes, or from about 25 minutes to about 35 minutes, or as otherwise prescribed. In embodiments, the process may be carried out with or without the use of creams or lotions on the scalp. In embodiments, the user may be able to walk around during the process—that is, in embodiments, the laser therapy apparatus is portable, and the user may be able to complete the irradiation process while doing other tasks.

During treatment, the laser therapy apparatus emits light, such as, in embodiments, monochromatic red light, from the light sources (including laser diodes and/or LEDs) to stimulate the scalp and provide energy to the hair follicles. Monochromatic red light is thought to increase blood circulation, improve cellular activity, and reverse the normal deterioration of cells. Improved respiration at the cellular level revitalizes hair to grow thicker and healthier. Thus, without being bound to any particular theory, laser therapy is thought to revitalize follicles that are producing fine, thinning vellus hair into healthier follicles that produce thicker, healthier terminal hair.

It will be appreciated by those skilled in the art that the present invention can be embodied in other specific forms without departing from the spirit or essential characteristics thereof. The presently disclosed embodiments are therefore considered in all respects to be illustrative and not restricted. Modifications and variations are possible in light of the above teachings or may be acquired from practicing of the disclosure, without departing from the breadth or scope.

I claim:

1. A laser therapy apparatus comprising:
   a cap body shell;
   a printed circuit board disposed within the cap body shell, wherein the printed circuit board comprises a plurality of non-angled cuts and angled cuts, each non-angled cut having two sides, each angled cut having a perimeter of at least four sides, and wherein the printed circuit board is bent into a dome shape;
   a power supply;
   a controller;
   a first plurality of light sources electrically coupled to the printed circuit board and powered by the power supply, wherein the first plurality of light sources comprises at least two laser diodes; and
   at least two photodiode proximity sensors disposed within the cap body shell and coupled to the controller, wherein the photodiode proximity sensors are configured such that the plurality of light sources will only light if the at least two photodiode proximity sensors are less than two inches away from the scalp and further configured to keep the plurality of light sources from lighting if any of the photodiode proximity sensors are moved more than 0.5 inches away from a scalp.

2. The laser therapy apparatus according to claim 1, wherein at least one of the at least two laser diodes emits 650 nm light.

3. The laser therapy apparatus according to claim 1, wherein the first plurality of light sources further comprises at least one light emitting diode.

4. The laser therapy apparatus according to claim 1, wherein the plurality of non-angled cuts and the angled cuts in the printed circuit board comprises at least two dogleg shaped cuts.

5. The laser therapy apparatus according to claim 1, further comprising a second plurality of light sources electrically connected to the printed circuit board and powered by the power supply wherein the second plurality of light sources comprises at least two light emitting diodes; and
   a controller generating lighting patterns using the first and second plurality of light sources, the lighting patterns being a sequence of activating and deactivating light sources of the first and second plurality of light sources.

6. The laser therapy apparatus according to claim 5, wherein the first plurality of light sources is controllable independently of the second plurality of light sources.

7. The laser therapy apparatus according to claim 1, wherein the laser therapy apparatus comprises at least 70 laser diodes.

8. The laser therapy apparatus according to claim 1, wherein the cap body shell comprises a clear window.

9. A hat including the laser therapy apparatus according to claim 1.

10. The laser therapy apparatus according to claim 1, further comprising a stand supporting the laser therapy apparatus.

11. The laser therapy apparatus according to claim 1, further comprising a second plurality of light sources electrically connected to the printed circuit board and powered by the power supply wherein the second plurality of light sources comprises at least two light emitting diodes.

12. The laser therapy apparatus of claim 11, wherein the second plurality of light sources comprises more in terms of lights sources having light emitting diodes than the first plurality of light sources having laser diodes.

13. The laser therapy apparatus of claim 11, wherein the first plurality of light sources and second plurality of light sources comprise a plurality of panels of light sources, each panel of light sources being separately controlled by the controller to provide lighting patterns.

14. A laser therapy apparatus comprising:
   a cap body shell;
   a printed circuit board disposed within the cap body shell, wherein the printed circuit board comprises a plurality of cuts, and wherein the printed circuit board is bent into a dome shape;
   a power supply;
   a controller;
   a first plurality of light sources electrically coupled to the printed circuit board and powered by the power supply, wherein the first plurality of light sources comprises at least two laser diodes; and
   at least two photodiode proximity sensors disposed within the cap body shell and coupled to the controller, wherein the photodiode proximity sensors are configured such that the plurality of light sources will only light if the at least two photodiode proximity sensors are less than two inches away from the scalp and further configured to keep the plurality of light sources from lighting if any of the photodiode proximity sensors are moved more than 0.5 inches away from a scalp.

15. The laser therapy apparatus of claim 14, wherein the at least two photodiode proximity sensors are configured and arranged having separation of at least a width of four fingers of an average human hand.

* * * * *